(12) United States Patent
Presura et al.

(10) Patent No.: US 10,405,760 B2
(45) Date of Patent: Sep. 10, 2019

(54) HEART RATE MONITOR SYSTEM

(71) Applicant: KONINKLIJKE PHILIPS N.V., Eindhoven (NL)

(72) Inventors: Cristian Nicolae Presura, Veldhoven (NL); David Antoine Christian Marie Roovers, Eindhoven (NL); Ruxandra Valentina Bobiti, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 143 days.

(21) Appl. No.: 15/125,234

(22) PCT Filed: Feb. 27, 2015

(86) PCT No.: PCT/EP2015/054133
§ 371 (c)(1),
(2) Date: Sep. 12, 2016

(87) PCT Pub. No.: WO2015/139930
PCT Pub. Date: Sep. 24, 2015

(65) Prior Publication Data
US 2017/0071489 A1    Mar. 16, 2017

(30) Foreign Application Priority Data

Mar. 17, 2014  (EP) .................................. 14160183
Mar. 26, 2014  (EP) .................................. 14161799

(51) Int. Cl.
*A61B 5/00*    (2006.01)
*A61B 5/08*    (2006.01)
(Continued)

(52) U.S. Cl.
CPC ...... *A61B 5/02416* (2013.01); *A61B 5/02438* (2013.01); *A61B 5/681* (2013.01);
(Continued)

(58) Field of Classification Search
CPC . A61B 5/02416; A61B 5/02438; A61B 5/681; A61B 5/6815; A61B 5/7203; A61B 5/721
See application file for complete search history.

(56) References Cited

U.S. PATENT DOCUMENTS

| 5,243,993 A | 9/1993 | Alexander et al. |
| 2008/0319281 A1 | 12/2008 | Aarts |

(Continued)

FOREIGN PATENT DOCUMENTS

| EP | 0913121 A1 | 5/1999 |
| EP | 1269911 A2 | 1/2003 |

(Continued)

OTHER PUBLICATIONS

Xiao, et al., "Heart Rate Prediction Model based on Physical Activities using Evolutionary Neural Network", IEEE Computer Society, 2010 Fourth International Conference on Genetic and Evolutionary Computing, pp. 198-201.

(Continued)

*Primary Examiner* — Paula J Stice

(57) ABSTRACT

A heart rate monitor system having at least one primary heart rate sensor (110) for measuring or determining a heart rate of a user and for outputting an output signal (HR) is provided. The output signal (HR) is based at least on measured heart beats and/or artifacts. The heart rate monitor system also comprises a model unit (132) for estimating or predicting a heart rate (HRM) of a user based on a model stored in the model unit (132) and the information received from at least one secondary sensor (120) measuring at least one physiological factor influencing heart rate of a user. The heart rate monitor system furthermore comprises a processing unit (131) for correlating the output signal (HR) received from the primary sensor (110) with the estimated or pre- (Continued)

dicted hear rate (HRM) received from the model unit (132) to differentiate the measured heart beats from the artifacts.

7 Claims, 3 Drawing Sheets

(51) Int. Cl.
*A61B 5/024* (2006.01)
*A61B 5/01* (2006.01)
*A61B 5/11* (2006.01)

(52) U.S. Cl.
CPC ............ *A61B 5/6815* (2013.01); *A61B 5/721* (2013.01); *A61B 5/7203* (2013.01); *A61B 5/01* (2013.01); *A61B 5/0816* (2013.01); *A61B 5/1118* (2013.01); *A61B 5/6823* (2013.01); *A61B 2503/10* (2013.01); *A61B 2562/0219* (2013.01)

(56) References Cited

U.S. PATENT DOCUMENTS

| | | |
|---|---|---|
| 2009/0048526 A1 | 2/2009 | Aarts et al. |
| 2009/0105602 A1 | 4/2009 | Gehman et al. |
| 2010/0030088 A1 | 2/2010 | Carney et al. |
| 2012/0172684 A1 | 7/2012 | Buchheim et al. |
| 2012/0283525 A1 | 11/2012 | Kuroda |
| 2013/0006123 A1 | 1/2013 | Aoshima |
| 2013/0178754 A1* | 7/2013 | Rulkov .............. A61B 5/02438 600/508 |
| 2014/0088443 A1 | 3/2014 | Van Den Heuvel et al. |
| 2016/0081630 A1 | 3/2016 | Aoshima |

FOREIGN PATENT DOCUMENTS

| | | |
|---|---|---|
| EP | 1297784 A1 | 4/2003 |
| EP | 2116183 A1 | 11/2009 |
| EP | 2520222 A1 | 11/2012 |
| WO | 2009023524 A1 | 2/2009 |
| WO | 2013036718 A1 | 3/2013 |
| WO | 2013038296 A1 | 3/2013 |
| WO | 2013128345 A1 | 9/2013 |
| WO | 2013143893 A1 | 10/2013 |

OTHER PUBLICATIONS

Hajek, et al., "Mathematical Model of Heart Rate Regulation During Exercise", Automatica, vol. 16, pp. 191-195.

Xu, et al., "An adaptive Kalman filter technique for context-aware heart rate monitoring", 34th Annual International Conference of the IEEE EMBS, San Diego, CA, Aug. 28,-Sep. 1, 2012, pp. 6522-6525.

* cited by examiner

HEART RATE MONITOR SYSTEM

CROSS-REFERENCE TO PRIOR APPLICATIONS

This application is the U.S. National Phase application under 35 U.S.C. § 371 of International Application No. PCT/EP2015/054133, filed on Feb. 27, 2015, which claims the benefit of European Patent Application No. 14161799.3, filed on Mar. 26, 2014 and European Patent Application No. 14160183.1, filed Mar. 17, 2014. These applications are hereby incorporated by reference herein, for all purposes.

FIELD OF THE INVENTION

The invention relates to a heart rate monitor system for measuring a heart rate of a user as well as a method for measuring a heart rate of a user.

BACKGROUND OF THE INVENTION

EP 1 269 911 A2 discloses a system and method for selecting physiological data from a plurality of physiological data sources. The system comprises several sensors and a selection algorithm which selects the measurements from one of the sensors and outputs the respective measurement results. A first sensor measures a physiological trait and a second sensor will also measure the physiological trait but with a different physiological characteristic. The selection algorithm selects that physiological data which provides a heart rate which is most suitable for the output. In particular, the measurement results from those sensors which have the greatest accuracy are selected.

EP 2 520 222 A1 discloses a biological information processing device. The biological information processing device has a sensor for measuring a pulse rate of a user and a detector for detecting a motion of a user. An estimation unit is provided for estimating a pulse based on the measurements of the motion detector. As long as a measurement of the pulse rate is possible, the output of the pulse rate sensor will be displayed. If the measurement is, however, not possible, then the estimated pulse rate as determined by the estimation unit will be displayed.

EP 2 116 183 A1 discloses a robust opto-electrical ear located cardiovascular monitoring device. The device comprises a first sensor based on a PPG technique for measuring a first cardiovascular signal and at least a second cardiovascular sensor based on an electrocardiography or an impedance cardiography method for measuring a second cardiovascular signal. The device further comprises a processing module for estimating the reliability of the cardiovascular sensor signals and selects one of the cardiovascular signals.

US 2012/0172684 A1 discloses a heart rate monitor having a heart rate sensor and a motion sensor. The motion sensor serves to detect a motion of a user. The detected motion is correlated in time with the signal from the hear rate sensor to provide a compensation signal in which the noise contribution due to motion is reduced.

The monitoring of a heart rate of a user for example by means of optical sensors is well known. Here, an optical sensor emits light into the skin of a user. The emitted light is scattered within the skin and reflected light exits the skin and is captured by an appropriate sensor. Based on the received signals from the sensor, the heart rate of a user can be determined.

Heart rate sensors are for example been used for fitness applications. These devices monitor the heart rate by means of chest belts or at the wrist or forearm of a user. As the heart rate monitor sensors are also used when the user is moving, in particular for fitness applications, the motion of the user can introduce motion artifacts in the measurements of the heart rate sensor. These motion artifacts may be considered as a heart beat such that the heart rate sensor can misinterpret these motion artifacts as heart beats leading to an incorrect heart rate.

EP 2 612 594 A2 discloses a heart rate monitor in form of a wrist watch type device. The heart rate monitor comprises an optical sensor for detecting the heart rate, a motion sensor for sensing changes in the position of the device with respect to the skin in order to compensate for noise. Furthermore, an accelerometer is provided to give information regarding the motion of the user with respect to the user's heart. A heart rate Kalman filter is used to compute a heart rate on the basis of signals obtained from the plurality of sensors.

SUMMARY OF THE INVENTION

It is an object of the present invention to provide a heart rate monitor system and a corresponding method which enable an improved accuracy and a more reliable monitoring of the actual rate of a user.

In an aspect of the present invention, a heart rate monitor system having at least one primary optical heart rate sensor for measuring or determining a heart rate of a user and for outputting an output signal is provided. The output signal is based at least on measured heart beats and/or artifacts. The heart rate monitor system also comprises a model unit for estimating or predicting a heart rate of a user based on a model stored in the model unit and the information received from at least one secondary sensor measuring at least one physiological factor influencing heart rate of a user. The heart rate monitor system furthermore comprises a processing unit for correlating the output signal received from the primary sensor with the estimated or predicted hear rate received from the model unit to differentiate the measured heart beats from the artifacts. By using the estimated or predicted heart rate from the model unit, those artifacts in the output signal of the primary heart rate sensor are identified and excluded from the output signal such that the actual heart rate of a user without substantially any artifacts can be obtained. Thus, the heart rate monitor system is more robust and reliable. As input of the model unit, the data from secondary sensors measuring at least one physiological factor influencing the heart rate of a user can be used.

According to a further aspect of the invention, the artifacts are motion artifacts created by relative motion between the at least one primary sensor and the user. By eliminating these artifacts from the output of the primary heart rate sensor, the heart rate monitoring system can be made more robust and reliable.

According to a further aspect of the invention, the primary sensor is an optical sensor which can optionally comprise a green light emitting diode.

According to a further aspect of the invention, the physiological factors influencing the heart rate measured by the secondary sensor are the breath of the user, the speed of the user, the acceleration of the user, the humidity on the skin of the user, the altitude of the user and/or the temperature of the user.

These physiological factors can be used as input for the model unit to estimate or predict an accurate heart rate of the user.

According to an aspect of the invention, the primary sensor is arranged in a wrist device, a chest belt or a device worn behind the ear of the user.

The invention also relates to a method of monitoring a heart rate of a user. The heart rate of a user is measured or determined and an output signal is outputted, wherein the output signal is based at least on measured heart beats and/or artifacts. A heart rate of a user is estimated or predicted based on a model stored in a model unit as well as information received from at least one secondary sensor measuring at least one physiological factor influencing a hear rate of a user. The output signals received from the primary sensor are correlated with the estimated or predicted heart rate received from the model unit to differentiate the measured beats from artifacts.

In an aspect of the invention, the at least one secondary sensor can be an internal or an external sensor with respect to the heart rate monitor system. In other words, the primary and secondary sensors can be arranged in a single housing or the at least one second sensor can be arranged outside the housing of the at least one first sensor. Accordingly, the at least one secondary sensor can be arranged adjacent to the first sensor or at another position. According to an aspect of the invention, a primary sensor, for example an optical sensor, is used to measure the heart rate of a user. A secondary sensor is used to measure or determine physiological factors that are influencing the heart rate of a user.

The invention also relates to a computer program for monitoring a heart rate of a user in a heart rate monitor system. The computer program comprises program code means for causing the heart rate monitor system to carry out steps of monitoring a heart rate of a user when the computer program is run on a computer controlling the heart rate monitor system.

These and other aspects of the invention will be apparent from and elucidated with reference to the embodiment(s) described hereinafter.

DETAILED DESCRIPTION OF EMBODIMENTS

Figure 1:
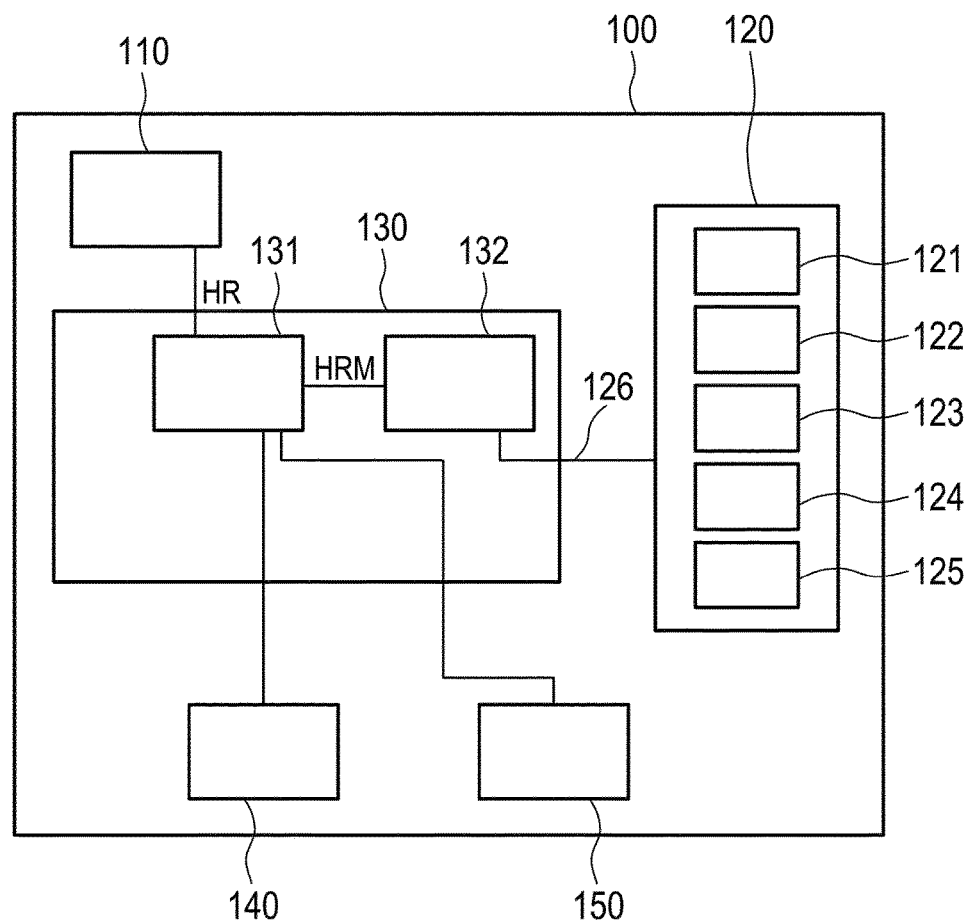
FIG. 1 shows a schematic block diagram of a heart rate monitor system according to the invention.

FIG. 1 shows a schematic block diagram of a heart rate monitor system according to the invention. The heart rate monitor system 100 comprises at least one primary sensor 110 for measuring a heart rate of a user, at least one secondary sensor 120 for measuring or determining at least one physiological factor influencing the heart rate of a user. A processing unit 131 for processing the output HR of the at least one primary sensor 110 to determine the heart rate HR of a user is provided. Optionally, the heart rate monitor system can comprise a display 140 for displaying the heart rate and/or an output 150 for outputting the measured or determined heart rate.

According to an aspect of the invention, the heart rate monitor system 100 can optionally be arranged at a wrist of a user, at a forearm or behind an ear of a user.

The primary sensor 110 can be implemented as an optical sensor which comprises a light source for example in form of a LED for producing artificial light. The light source emits the artificial light onto the skin of a user. Within the skin, the emitted artificial light is partially absorbed by the blood within the blood vessels and the artificial light can be scattered throughout the skin and can be reflected back to a photo detector which may also be part of the optical sensor 110. The photo detector is detecting the reflected light through the skin of the user and is generating an output signal. The output signal HR of the optical sensor 110 can be forwarded to the processing unit 131. Optionally, the processing unit 131 can also be arranged in the optical sensor 110. The processing unit 131 receives the output signal HR from the optical sensor 110 and determines a pulse rate or a heart rate of the user based on the output signal of the primary sensor 110.

The heart rate monitor system 100 furthermore comprises a model unit 132. In the model unit 132, a model is stored which represents the relationship between physical activity of a user and the heart rate of a user. The at least one secondary sensor 120 outputs a signal 126 indicating the physical activity of the user to the model unit 132. Based on the physical activity or the activity level of a user, a heart rate HRM is estimated or predicted by the model unit 132. The estimated heart rate HRM is forwarded to the processing unit 131 which compares the estimated heart rate HRM with the output signal HR from the primary sensor 110. If the output signal from the primary sensor 110 may comprise several candidates for a possible heart rate (for example due to artifacts in the output signal), the processing unit 131 compares the possible candidates for the heart rate with the estimated or predicted heart rate HRM and selects that heart rate that corresponds best to the predicted or estimated heart rate.

The model unit 132 and/or the processing unit 131 can be embodied in a microcontroller or a computer 130.

Figure 2:
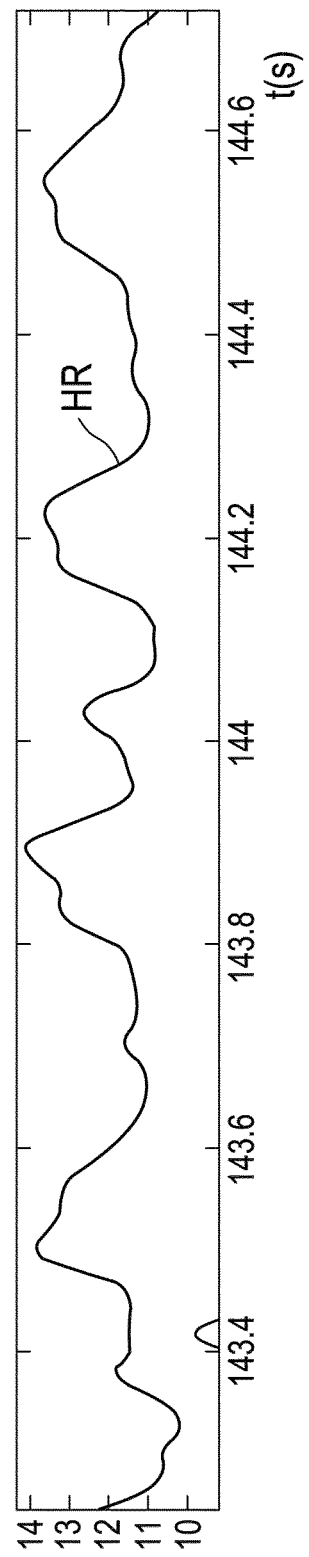
FIG. 2 shows a graph indicating an output of a heart rate sensor as a function of time.

FIG. 2 shows a graph indicating an output of a heart rate sensor as a function of time. In FIG. 2, an output signal HR of the heart rate sensor (i.e. the primary sensor) 110 as a function of time is depicted. Here, several peaks can be shown in the output signal HR of the sensor 110. These peaks can, however, be related to an actual heart beat, to motion artifacts or a combination of these. FIG. 2 in particular shows the function of the output signal HR of the heart rate sensor 110 as a function of time in the temporal domain. In particular, those peaks that appear regularly in the output signal of the heart rate sensor can correspond to heart beats of a user. The actual heart rate is then determined by counting the number of pulses (of a heart beat) within a second.

However, due to motion artifacts, not only the peaks relating to a heart beat will occur but also motion artifacts. The frequency of those peaks that are related to motion artifacts may relate to the frequency of the movement, e.g. the movement of an arm during sport. In particular, such peaks may be mistakenly taken as peaks relating to heart beats of the user. Therefore, a case can occur where the output signal HR can comprise different candidates for heart beats and therefore different heart rates may be present in the output signal.

According to an aspect of the invention, the analysis of the output signals HR of the heart rate sensor 110 can be performed based on an auto-correlation function of subsequent data segments. Here, one of the peaks in the auto-correlation function is then selected as relating to a heart beat and thus the heart rate can be calculated. Due to the presence of motion artifacts, the selection of the correct peak which corresponds to a heart beat can be difficult as several possible peaks can be present in the data. The assumption that the highest peak will also correspond to a heart beat is not always true.

Accordingly, due to the presence of the heart beat as well as possible motion or other artifacts, several peaks can be present in the output signal HR of the heart rate sensor 110. The heart rate system according to an aspect of the invention now determines how to select the correct peak which corresponds to a heart beat from among possibly multiple peaks in the output signal of the heart rate sensor.

It is well known that the heart rate of a person is dependent on several factors like the physical condition of the user, the motion rate, the activity of the user, the emotional condition of the user as well as internal and external factors. By means of the secondary sensors 120, information can be gathered which relate to factors which have an influence on the heart rate. The physiological factors that can be measured by the secondary sensors are e.g. breath, speed of the user, acceleration of the user, humidity on the skin of the user, altitude, etc.

The heart rate monitoring system according to an aspect of the invention uses the knowledge of this dependency to create a model of the heart rate of a user. The model of a heart rate with respect to the activity level can for example the following first order auto-regressive model:

$$HR(t) = HR_0 + HR_A(t)$$

$$HR_A(t) = \alpha * HR_A(t-1) + \beta * A(t-1)$$

HR(t) corresponds to the heart rate at a point of time t. $HR_0$ corresponds to the heart rate at rest. $HR_A$ corresponds to the contribution of the activity to the heart rate. A(t) corresponds to the activity level of the user at the time t.

The two parameters $\alpha$, $\beta$ can be fixed or can be adapted according to user specific parameters, the current activity type as well as other external factors. Preferably, the adaption or calibration of the two parameters $\alpha$, $\beta$ is performed when an accurate heart rate measurement is possible.

Figure 3:
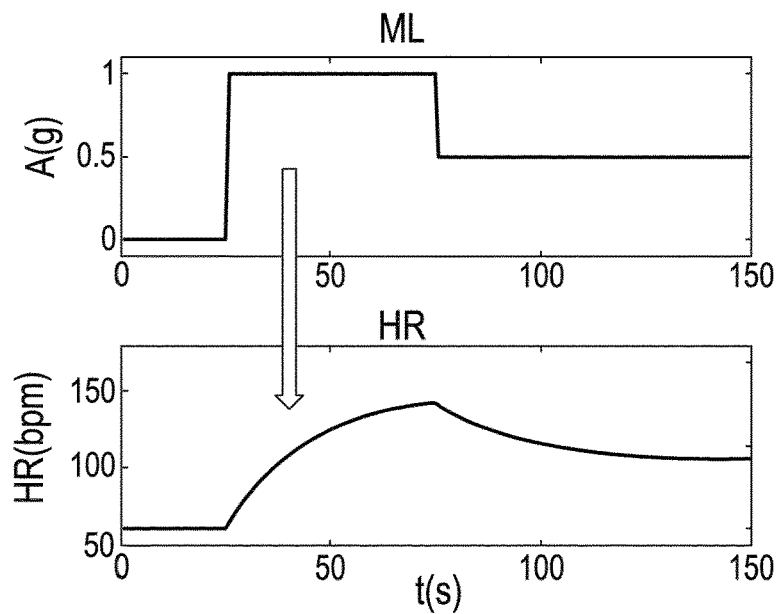
FIG. 3 shows a schematic graph indicating an application of the heart rate monitoring method according to an embodiment of the invention.

FIG. 3 shows a schematic graph indicating an application of the heart rate monitoring method according to an aspect of the invention. In FIG. 3, a motion level ML as well as a predicted heart rate HR is shown. In FIG. 3, the motion level ML as acceleration A(g) over time as well as the heart rate as beats per minute bpm are also depicted over time.

According to an aspect of the invention, the secondary sensors 120 can be used to determine the activity level of the user such that based on this activity level, the model unit 132 can estimate or predict a heart rate HRM of a user. In some cases, the estimated or predicted heart rate HRM of the user as predicted or estimated by the model unit 132 can be accurate. However, also other cases may be present where this is not true and the predicted or estimated heart rates do not correspond to the actual heart rate of the user. It should be noted that the above described model is merely a simple model with its limitations. In particular, the accuracy of this model which is based on a prediction of the heart rate based on the movement and physical effort of the user. In addition, having for example only motion sensors or acceleration sensors in for example a wrist device does not enable an accurate or direct measurement of the physical effort of the user. For example the movement of a wrist as detected by the motion and/or acceleration sensors does not necessarily correlate to the movement of the user which indicates the physical effort of the user.

According to an aspect of the invention, the predicted or estimated heart rate HRM of the model unit 132 is used to verify the output HR of the heart rate sensor 110. In other words, the estimated or predicted heart rate HRM is used to determine which heart rate is the actual heart rate of a user. Thus, with the estimated or predicted heart rate HRM from the model unit 132, it is possible to eliminate those possible heart rates which do not correspond to the actual heart rate but rather for example to motion artifacts or the like.

Figure 4:
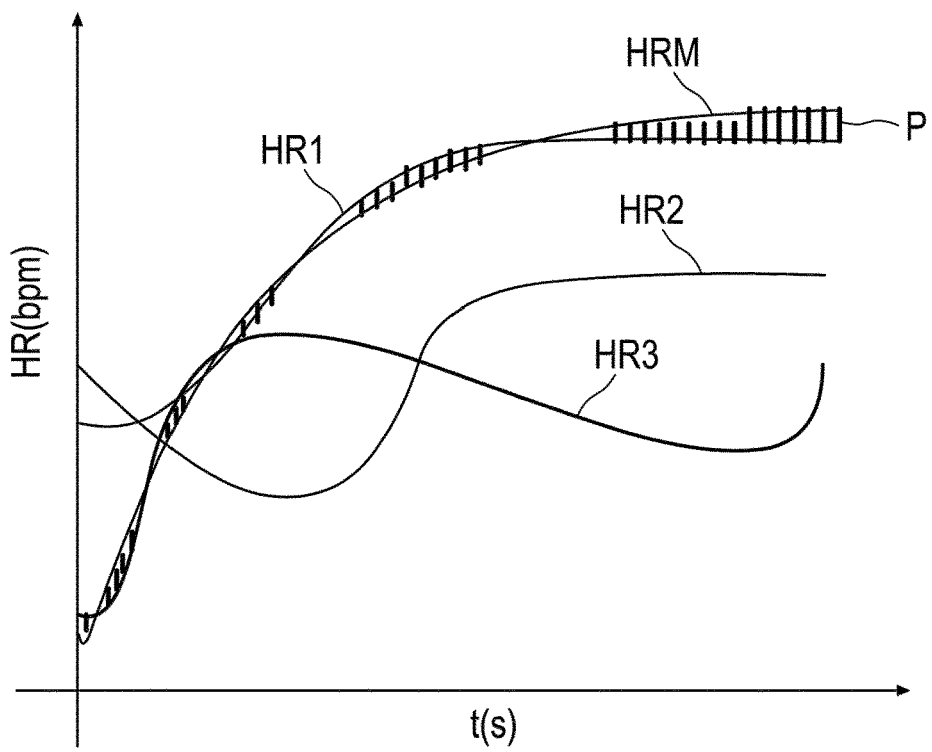
FIG. 4 shows a graph indicating the heart rate over time according to an embodiment of the invention.

FIG. 4 shows a graph indicating the heart rate over time according to an embodiment of the invention. In FIG. 4, three different possible heart rates HR1, HR2, HR3 in beats per minute are shown over time t. Furthermore, the predicted or estimated heart rate HRM as predicted or estimated by the model unit 132 is also shown over time. According to an aspect of the invention, the predicted or estimated heart rate HRM is compared to the three possible heart rates HR1, HR2, HR3. In FIG. 4, also a plurality of pointers P is depicted which based from the predicted or estimated heart rate HRM point towards the closest candidate, in this case the heart rate HR1. Accordingly, with the additional information from the predicted or estimated heart rate HRM, a heart rate monitor system can select the correct heart rate from among a set of different hear rates.

According to a further aspect of the invention, a camera can be used as optical sensor to determine the heart rate. According to this aspect of the invention, a user may use a fitness device such as a treadmill, a rowing machine, etc. A power meter in or on the fitness device can be used to determine the actual activity level of the user. Such a power meter can be a sensor mounted on a gym bicycle that measures the power with which the user pushes the wheel of the bicycle. It can also be the speed measured by the treadmill. According to this aspect of the invention, a model can be constructed between the power used by the device and the heart rate. Such a model may provide some expectation values of the heart rate, as a function of power. These expectation values may be used later to choose the heart rate candidates.

The use of the basic concept of the invention can be detected if the optical signal from an optical sensor of a device is compared to the output of an optical sensor without the use of the model unit to select one heart rate from among a set of possible heart rates.

According to the invention, the primary sensor can be an optical sensor which can for example use a green light emitting diode. According to the invention, the secondary sensors can be located in close proximity to the primary sensor but can also be located at different positions.

According to an aspect of the invention, the secondary sensors 120 can be a humidity sensor 121, an altimeter 122, a GPS sensor 123, an accelerometer 124 and/or a pressure sensor 125. The humidity sensor 121 can be used to measure the humidity on the skin of a user. The humidity on the skin of the user can be a parameter indicating emotions, physiological conditions of the user and changes in the mood. The altimeter 122 can for example be used to determine the altitude of the user. This may give an indication whether the user is gliding, climbing, etc. The GPS sensor 123 can be used as a speed sensor for example thus determining whether the user is cycling, racing, etc.

The pressure sensor 125 can be an air pressure meter, which can be seen also as an altimeter. When the air pressure is high, there may be persons that react to it with an elevated heart rate.

According to an aspect of the invention, the heart rate monitor system comprises a model unit 132. The outputs 126 of the secondary sensors 120 are received by the model unit 132 and based on a model which is stored in the model unit 132, a heart rate is predicted or estimated based on the information from the secondary sensors 120.

According to the invention, the heart rate monitor system can have a housing which accommodates the primary sensor 110 as well as the at least one secondary sensor 120. However, alternatively, the secondary sensors 120 can be arranged outside of a housing of the primary sensor 110. For example, some of the secondary sensors 120 may be part of an external device like a smartphone etc. The secondary sensors 120 may also be arranged at other parts of the body as the housing of the primary sensor 110.

The heart rate monitor system can be arranged as a wrist device. The heart rate monitor system can also be arranged as a device worn at or on an ear of the user. The heart rate monitoring system may also be part of glasses worn by the user. The heart rate monitor system may also be part of a hearing aid worn by the user.

The primary sensor 110 can be embodied as an optical sensor, an electrical sensor and/or a pressure sensor. The secondary sensors can be embodied as a humidity sensor, a speed sensor, an acceleration sensor, an altimeter, etc. Preferably, the secondary sensors have a power consumption that is lower than the power consumption of the primary sensor.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

A computer program may be stored and/or distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A heart rate monitor system, comprising:
   at least one primary optical heart rate sensor configured to measure a heart rate of a user and generate output signals (HR), wherein the output signals (HR) are based at least on measured heart beats and measured artefacts;
   a model unit configured to predict an estimated heart rate (HRM) of the user based on a model stored in the model unit and information received from at least one secondary sensor measuring at least one physiological factor influencing the heart rate of the user, the model representative of a relationship between physical activity of the user and the heart rate of the user, and
   a processor configured to compare the output signals (HR) received from the at least one primary optical heart rate sensor with the estimated heart rate (HRM) received from the model unit to differentiate the measured heart beats from the measured artefacts and output a determined heart rate.

2. The heart rate monitor system according to claim 1, wherein the measured artifacts are motion artifacts created by a relative motion between the at least one primary optical heart rate sensor and the user.

3. The heart rate monitor system according to claim 1, wherein the at least one primary optical heart rate sensor comprises a green light emitting diode.

4. The heart rate monitor system according to claim 1, wherein the at least one physiological factor influencing the heart rate measured by the at least one secondary sensor comprises breath of the user, speed of the user, acceleration of the user, humidity on skin of the user, altitude of the user and/or temperature of the user.

5. The heart rate monitor system according to claim 1, wherein the at least one primary optical heart rate sensor is arranged at a wrist of the user, at a forearm of the user, or behind an ear of the user.

6. Computer A computer program for monitoring a heart rate of a user in the heart rate monitor system as defined in claim 1, the computer program comprising program code means for causing the heart rate monitor system to carry out the steps of: measuring a heart rate of a user by a primary optical heart rate sensor and outputting output signals (HR), wherein the output signals are based at least on measured heart beats and measured artefacts; predicting an estimated heart rate (HRM) of the user based on a model stored in a model unit and information received from at least one secondary sensor measuring at least one physiological factor influencing the heart rate of the user, the model representative of a relationship between physical activity of the user and the heart rate of the user; and comparing the output signals (HR) received from the at least one primary optical heart rate sensor with the estimated heart rate (HRM) received from the model unit to differentiate the measured heart beats from the measured artifacts and outputting a determined heart rate, when the computer program is run on a computer controlling the heart rate monitor system.

7. A method of monitoring a heart rate of a user, comprising the steps of:
   measuring a heart rate of a user by a primary optical heart rate sensor and outputting output signals (HR), wherein the output signals are based at least on measured heart beats and measured artefacts;
   predicting an estimated heart rate (HRM) of the user based on a model stored in a model unit and information received from at least one secondary sensor measuring at least one physiological factor influencing the heart rate of the user, the model representative of a relationship between physical activity of the user and the heart rate of the user; and
   comparing, by a processor, the output signals (HR) received from the at least one primary optical heart rate sensor with the estimated heart rate (HRM) received from the model unit to differentiate the measured heart beats from the measured artifacts and outputting a determined heart rate.

* * * * *